United States Patent
Grey

(10) Patent No.: US 6,441,204 B1
(45) Date of Patent: Aug. 27, 2002

(54) DIRECT EPOXIDATION PROCESS USING A MIXED CATALYST SYSTEM

(75) Inventor: Roger A. Grey, West Chester, PA (US)

(73) Assignee: Arco Chemical Technology, L.P., Greenville, DE (US)

( * ) Notice: Subject to any disclaimer, the term of this patent is extended or adjusted under 35 U.S.C. 154(b) by 0 days.

(21) Appl. No.: 10/045,888

(22) Filed: Oct. 19, 2001

(51) Int. Cl.⁷ .............................................. C07D 301/06
(52) U.S. Cl. ...................................... 549/533; 549/532
(58) Field of Search ................................. 549/533, 532

(56) References Cited

U.S. PATENT DOCUMENTS

| | | | |
|---|---|---|---|
| 3,351,635 A | 11/1967 | Kollar | 260/348.5 |
| 4,367,342 A | 1/1983 | Wulff et al. | 549/529 |
| 4,833,260 A | 5/1989 | Neri et al. | 549/531 |
| 5,496,532 A | 3/1996 | Monzen et al. | 423/584 |
| 5,623,090 A | 4/1997 | Haruta et al. | 568/360 |
| 6,008,388 A | 12/1999 | Dessau et al. | 549/531 |
| 6,307,073 B1 | 10/2001 | Jones | 549/532 |

FOREIGN PATENT DOCUMENTS

| | | |
|---|---|---|
| JP | 4-352771 | 12/1992 |
| WO | WO 98/00413 | 6/1997 |

*Primary Examiner*—Ba K. Trinh
(74) *Attorney, Agent, or Firm*—Kevin M. Carroll

(57) ABSTRACT

The invention is a liquid-phase process for epoxidizing an olefin with hydrogen and oxygen in the presence of a catalyst mixture comprising a titanium zeolite and a supported catalyst comprising palladium on niobium-containing support. The process is highly selective and productive for transforming olefins to epoxides in the liquid-phase reaction of an olefin, hydrogen, and oxygen.

20 Claims, No Drawings

US 6,441,204 B1

DIRECT EPOXIDATION PROCESS USING A MIXED CATALYST SYSTEM

FIELD OF THE INVENTION

This invention relates to a liquid-phase epoxidation process using a mixed catalyst system to produce epoxides from hydrogen, oxygen, and olefins. The mixed catalyst system contains a titanium zeolite and to palladium on a niobium-containing support.

BACKGROUND OF THE INVENTION

Many different methods for the preparation of epoxides have been developed. Generally, epoxides are formed by the reaction of an olefin with an oxidizing agent in the presence of a catalyst. The production of propylene oxide from propylene and an organic hydroperoxide oxidizing agent, such as ethyl benzene hydroperoxide or tert-butyl hydroperoxide, is commercially practiced technology. This process is performed in the presence of a solubilized molybdenum catalyst, see U.S. Pat. No. 3,351,635, or a heterogeneous titania on silica catalyst, see U.S. Pat. No. 4,367,342. Hydrogen peroxide is another oxidizing agent useful for the preparation of epoxides. Olefin epoxidation using hydrogen peroxide and a titanium silicate zeolite is demonstrated in U.S. Pat. No. 4,833,260. One disadvantage of both of these processes is the need to pre-form the oxidizing agent prior to reaction with olefin.

Another commercially practiced technology is the direct epoxidation of ethylene to ethylene oxide by reaction with oxygen over a silver catalyst. Unfortunately, the silver catalyst has not proved very useful in epoxidation of higher olefins. Therefore, much current research has focused on the direct epoxidation of higher olefins with oxygen and hydrogen in the presence of a catalyst. In this process, it is believed that oxygen and hydrogen react in situ to form an oxidizing agent. Thus, development of an efficient process (and catalyst) promises less expensive technology compared to the commercial technologies that employ pre-formed oxidizing agents.

Many different catalysts have been proposed for use in the direct epoxidation of higher olefins. For liquid-phase reactions, the catalysts typically contain palladium on a titanium zeolite support. For example, JP 4-352771 discloses the epoxidation of propylene oxide from the reaction of propylene, oxygen, and hydrogen using a catalyst containing a Group VIII metal such as palladium on a crystalline titanosilicate. The vapor-phase oxidation of olefins has been shown to produce epoxides over gold supported on titanium oxide ($Au/TiO_2$ or $Au/TiO_2$–$SiO_2$), see for example U.S. Pat. No. 5,623,090, and gold supported on titanosilicates, see for example PCT Intl. Appl. WO 98/00413.

Mixed catalyst systems for olefin epoxidation with hydrogen and oxygen have also been disclosed. For example, JP 4-352771 at Example describes the use of a mixture of titanosilicate and Pd/C for propylene epoxidation. U.S. Pat. No. 6,008,388 also describes a catalyst in which palladium is typically added to a titanium zeolite to form a catalyst system, but additionally teaches that the palladium can be incorporated into a support before mixing with the zeolite. However, the only supports that are disclosed include silica, alumina, and activated carbon. In addition, copending Appl. Ser. No. 09/624,942 discloses a mixed catalyst system that is useful in olefin epoxidation comprising a titanium zeolite and a gold-containing supported catalyst.

One disadvantage of the described direct epoxidation catalysts is that they all show either less than optimal selectivity or productivity. An additional disadvantage is that they are prone to ring-open under standard reaction conditions to form less desirable ring-opened products such as glycols or glycol ethers. As with any chemical process, it is desirable to develop new direct epoxidation methods and catalysts.

In sum, new processes for the direct epoxidatioh of olefins are needed. Especially desirable are new catalyst systems that are useful in the process. I have discovered an effective, convenient epoxidation process using a mixed catalyst system that gives good productivity and selectivity to epoxide.

SUMMARY OF THE INVENTION

The invention is an olefin epoxidation process that comprises reacting an olefin, oxygen, and hydrogen in an oxygenated solvent in the presence of a catalyst mixture comprising a titanium zeolite and a supported catalyst comprising palladium on a niobium-containing support. The new catalyst mixture is useful in the epoxidation of olefins with hydrogen and oxygen.

DETAILED DESCRIPTION OF THE INVENTION

The process of the invention employs a catalyst mixture that comprises a titanium zeolite and a supported catalyst comprising palladium and a support, wherein the support is a niobium-containing inorganic oxide. Suitable titanium zeolites are those crystalline materials having a porous molecular sieve structure with titanium atoms substituted in the framework. The choice of titanium zeolite employed will depend upon a number of factors, including the size and shape of the olefin to be epoxidized. For example, it is preferred to use a relatively small pore titanium zeolite such as a titanium silicalite if the olefin is a lower aliphatic olefin such as ethylene, propylene, or 1-butene. Where the olefin is propylene, the use of a TS-1 titanium silicalite is especially advantageous. For a bulky olefin such as cyclohexene, a larger pore titanium zeolite such as a titanium zeolite having a structure isomorphous with zeolite beta may be preferred.

Titanium zeolites comprise the class of zeolitic substances wherein titanium atoms are substituted for a portion of the silicon atoms in the lattice framework of a molecular sieve. Such substances are well known in the art.

Particularly preferred titanium zeolites include the class of molecular sieves commonly referred to as titanium silicalites, particularly "TS-1" (having an MFI topology analogous to that of the ZSM-5 aluminosilicate zeolites), "TS-2" (having an MEL topology analogous to that of the ZSM-11 aluminosilicate zeolites), and "TS-3" (as described in Belgian Pat. No. 1,001,038). Titanium-containing molecular sieves having framework structures isomorphous to zeolite beta, mordenite, ZSM48, ZSM-12, and MCM-41 are also suitable for use. The titanium zeolites preferably contain no elements other than titanium, silicon, and oxygen in the lattice framework, although minor amounts of boron, iron, aluminum, sodium, potassium, copper and the like may be present.

Preferred titanium zeolites will generally have a composition corresponding to the following empirical formula $xTiO_2$ $(1-x)SiO_2$ where x is between 0.0001 and 0.5000. More preferably, the value of x is from 0.01 to 0.125. The molar ratio of Si:Ti in the lattice framework of the zeolite is advantageously from 9.5:1 to 99:1 (most preferably from 9.5:1 to 60:1). The use of relatively titanium-rich zeolites may also be desirable.

The catalyst mixture employed in the process of the invention also contains a supported catalyst. The supported catalyst comprises palladium and a support, wherein the support is a niobium-containing inorganic oxide. Suitable niobium-containing inorganic oxide supports include niobium oxides and niobium mixed oxides. Niobium oxides include oxides of niobium wherein the valency of niobium is 2 to 5. Suitable niobium oxides include such oxides as NbO, $Nb_2O_3$, $NbO_2$, and $Nb_2O_5$. Niobium mixed oxides such as niobium oxide-silica, niobium oxide-alumina, and niobium oxide-titania may also be used. The amount of niobium present in the support is preferably in the range of from about 0.1 to about 86 weight percent. Preferred niobium-containing inorganic oxide supports include $Nb_2O_5$ and niobium oxide-silica.

The catalyst employed in the process of the invention also contains palladium. The typical amount of palladium present in the catalyst will be in the range of from about 0.01 to 20 weight percent, preferably 0.01 to 10 weight percent. The manner in which the palladium is incorporated into the catalyst is not considered to be particularly critical. For example, the palladium (for example, Pd tetraamine bromide) may be supported on the niobium-containing inorganic oxide support by impregnation, adsorption, ion-exchange, precipitation, or the like.

There are no particular restrictions regarding the choice of palladium compound used as the source of palladium. For example, suitable compounds include the nitrates, sulfates, halides (e.g., chlorides, bromides), carboxylates (e.g. acetate), and amine complexes of palladium.

Similarly, the oxidation state of the palladium is not considered critical. The palladium may be in an oxidation state anywhere from 0 to +4 or any combination of such oxidation states. To achieve the desired oxidation state or combination of oxidation states, the palladium compound may be fully or partially pre-reduced after addition to the catalyst. Satisfactory catalytic performance can, however, be attained without any pre-reduction.

After catalyst formation, the catalyst may be optionally thermally treated in a gas such as nitrogen, helium, vacuum, hydrogen, oxygen, air, or the like. The thermal treatment temperature is typically from about 50 to about 550° C.

Examples of catalysts comprising palladium and a niobium-containing inorganic oxide support are known. For instance, palladium on niobia catalysts have been disclosed for production of hydrogen peroxide (see, for example, U.S. Pat. No. 5,496,532).

The titanium zeolite and the supported catalyst may be used in the epoxidation process as a mixture of powders or as a mixture of pellets. In addition, the titanium zeolite and supported catalyst may also be pelletized or extruded together prior to use in epoxidation. If pelletized or extruded together, the catalyst mixture may additionally comprise a binder or the like and may be molded, spray dried, shaped or extruded into any desired form prior to use in epoxidation. The weight ratio of titanium zeolite:supported catalyst is not particularly critical. However, a titanium zeolite:supported catalyst ratio of 0.01–100 (grams of titanium zeolite per gram of supported catalyst) is preferred.

The process of the invention comprises contacting an olefin, oxygen, and hydrogen in an oxygenated solvent in the presence of the catalyst mixture. Suitable olefins include any olefin having at least one carbon-carbon double bond, and generally from 2 to 60 carbon atoms. Preferably the olefin is an acyclic alkene of from 2 to 30 carbon atoms; the process of the invention is particularly suitable for epoxidizing $C_2$–$C_6$ olefins. More than one double bond may be present, as in a diene or triene for example. The olefin may be a hydrocarbon (i.e., contain only carbon and hydrogen atoms) or may contain functional groups such as halide, carboxyl, hydroxyl, ether, carbonyl, cyano, or nitro groups, or the like. The process of the invention is especially useful for converting propylene to propylene oxide.

The process of the invention also requires the use of an oxygenated solvent. Oxygenated solvents may be any chemical that is a liquid under reaction conditions that contains at least one oxygen atom in its chemical structure. Suitable oxygenated solvents include water and oxygen-containing hydrocarbons such as alcohols, ethers, esters, ketones, and the like. Preferred oxygenated solvents include lower aliphatic $C_1$–$C_4$ alcohols such as methanol, ethanol, isopropanol, and tertbutanol, or mixtures thereof, and water. Fluorinated alcohols can be used. A preferred solvent is water. It is also possible to use mixtures of the cited alcohols with water.

Preferably, the process of the invention will also use buffers. If used, the buffer will typically be added to the solvent to form a buffer solution. The buffer solution is employed in the reaction to inhibit the formation of glycols during epoxidation. Buffers are well known in the art.

Suitable buffers include any suitable salts of oxyacids, the nature and proportions of which in the mixture, are such that the pH of their solutions may range from 3 to 10, preferably from 4 to 9 and more preferably from 5 to 8. Suitable salts of oxyacids contain an anion and cation. The anion portion of the salt may include anions such as phosphate, carbonate, acetate, citrate, borate, phthalate, silicate, aluminosilicate, or the like. The cation portion of the salt may include cations such as ammonium, alkylammoniums (e.g., tetraalkylammoniums), alkali metals, alkaline earth metals, or the like. Cation examples include $NH_4$, $NBu_4$, Li, Na, K, Cs, Mg, and Ca cations. More preferred buffers include alkali metal phosphate buffers. Buffers may preferably contain a combination of more than one suitable salt. Typically, the concentration of buffer is from about 0.0001 M to about 1 M, preferably from about 0.001 M to about 0.1 M, and most preferably from about 0.005 M to about 0.05 M.

Oxygen and hydrogen are also required for the process of the invention. Although any sources of oxygen and hydrogen are suitable, molecular oxygen and molecular hydrogen are preferred. The molar ratio of hydrogen to oxygen can usually be varied in the range of $H_2:O_2$=1:100 to 5:1 and is especially favorable at 1:5 to 2:1. The molar ratio of oxygen to olefin is usually 1:1 to 1:20, and preferably 1:1.5 to 1:10. Relatively high oxygen to olefin molar ratios (e.g., 1:1 to 1:3) may be advantageous for certain olefins.

In addition to olefin, oxygen and hydrogen, an inert gas carrier may be preferably used in the process. As the carrier gas, any desired inert gas can be used. Suitable inert gas carriers include noble gases such as helium, neon, and argon in addition to nitrogen and carbon dioxide. Saturated hydrocarbons with 1–8, especially 1–6, and preferably with 1–4 carbon atoms, e.g., methane, ethane, propane, and n-butane, are also suitable. Nitrogen and saturated $C_1$–$C_4$ hydrocarbons are the preferred inert carrier gases. Mixtures of the listed inert carrier gases can also be used. The molar ratio of olefin to carrier gas is usually in the range of 100:1 to 1:10 and especially 20:1 to 1:10.

Specifically in the epoxidation of propylene according to the invention, propane can be supplied in such a way that, in the presence of an appropriate excess of carrier gas, the explosive limits of mixtures of propylene, propane, hydrogen, and oxygen are safely avoided and thus no explosive mixture can form in the reactor or in the feed and discharge lines.

The amount of catalyst used may be determined on the basis of the molar ratio of the titanium contained in the titanium zeolite to the olefin that is supplied per unit time. Typically, sufficient catalyst is present to provide a titanium/olefin per hour molar feed ratio of from 0.0001 to 0.1.

For the liquid-phase process of the invention, the catalyst is preferably in the form of a suspension or fixed-bed. The process may be performed using a continuous flow, semi-batch or batch mode of operation. It is advantageous to work at a pressure of 1–100 bars. Epoxidation according to the invention is carried out at a temperature effective to achieve the desired olefin epoxidation, preferably at temperatures in the range of 0–250° C., more preferably, 20–200° C.

The following examples merely illustrate the invention. Those skilled in the art will recognize many variations that are within the spirit of the invention and scope of the claims.

EXAMPLE 1

PREPARATION OF $Pd/Nb_2O_5$ CATALYST

Catalyst 1A:1 wt. % Palladium on Niobium Oxide

In a glass beaker, $Pd(NH_3)_4Br_2$ (0.64 g) is dissolved in 40 grams of deionized water. In a separate beaker, niobium oxide powder (20 g, from Reference Metals) is slurried in 90 grams of deionized water. The palladium salt solution is added to the niobium oxide slurry with stirring over a 10-minute period. The resulting slurry is stirred at 23° C. for two hours, then the solids are separated by centrifuge. The solids are washed four times by slurrying in 80 grams of water and centrifuging. The solids are then dried in a vacuum oven (1 torr) at 50° C. for 4 hours to give 14.6 grams of Catalyst 1A. Elemental analysis showed palladium=1.01 wt. %, bromide=1.6 wt. %, nitrogen 0.22 wt. % and niobium=68 wt %.

Catalyst 1B: 0.5 wt. % Palladium on Niobium Oxide

The procedure of Catalyst 1A is repeated except that 0.24 grams of $Pd(NH_3)_4Br_2$ (in 30 grams of deionized water) and 15 grams of niobium oxide powder are used. The preparation resulted in the isolation of 9.6 grams of Catalyst 1B. Elemental analysis showed palladium=0.51 wt. %, bromide=0.72 wt. %, nitrogen<0.1 wt. % and niobium=68 wt. %.

Catalyst 1C: 1 wt. % Pd on Niobium Oxide from $Pd(NH_3)_4(NO_3)_2$

In a glass beaker, $Pd(NH_3)_4(NO_3)_2$ (3.5 g, of an solution containing 10% $Pd(NH_3)_4(NO_3)_2$ is mixed with 16 grams of deionized water. In a eparate beaker, niobium oxide powder (12.5 g, from Reference Metals) is slurried in 40 grams of deionized water. The palladium salt solution is added to the niobium oxide slurry with stirring over a 20-minute period. The resulting slurry is stirred at 23° C. for two hours, then the solids are separated by centrifuge. The solids are washed four times by slurrying in 80 grams of water and centrifuging. The solids are then dried in a vacuum oven (1 torr) at 50° C. for 4 hours to give to give 8.6 grams of Catalyst 1C. Elemental analysis showed palladium=0.99 wt %, nitrogen 0.18 wt % and niobium=68 wt %.

EXAMPLE 2

EPOXIDATION OF PROPYLENE USING TS-1 and $Pd/Nb_2O_5$ MIXTURE

TS-1 can be made according to any known literature procedure. See, for example, U.S. Pat. No. 4,410,501, DiRenzo, et. al., Microporous Materials (1997), Vol. 10, 283, or Edler, et. al., J. Chem. Soc., Chem. Comm. (1995), 155. The TS-1 is calcined at 550° C. for 4 hours before use.

Cesium phosphate buffer is first produced according to the following procedure. Cesium hydroxide (22.12 g) is dissolved in deionized water (17.25 g) in a plastic beaker. In a separate container, 85% phosphoric acid (5.85 g) is added with cooling to 400 grams of deionized water. Twenty-five grams of the cesium hydroxide solution is carefully added to the phosphoric acid solution. After the addition, enough deionized water is added to the cesium phosphate buffer to give a volume of 500 mL. The pH of the solution is measured to be 6.9. Two hundred and twenty grams of the above solution (pH=6.9) is then treated with 85% phosphoric acid (1.01 g) to give a cesium phosphate buffer solution with a pH=6.02.

Run 2A: Epoxidation using Catalyst 1A and TS-1 with a Cesium Phosphate Buffer

A 300 cc stainless steel reactor is charged with Catalyst 1A (0.2 g), TS-1 (0.5 g, titanium amount=1.6 weight %), deionized water (117 g), and 13 grams of a buffer (0.1 molar cesium phosphate, pH=6 as prepared above). The reactor is then charged to 200 psig with a feed consisting of 4% hydrogen, 4% oxygen, 5% propylene, 0.5% methane and the balance nitrogen. The pressure in the reactor is maintained at 200 psig via a backpressure regulator with the feed gases passed continuously through the reactor at 1480 cc/min (measured at 23° C. and one atmosphere pressure). In order to maintain a constant solvent level in the reactor during the run, the oxygen, nitrogen and propylene feeds are passed through a two-liter stainless steel vessel (saturator) preceding the reactor, containing 1.5 liters of water. The reactor is stirred at 1600 rpm. The reaction mixture is heated to 60° C. and the gaseous effluent is analyzed by an online GC every hour and the liquid analyzed by offline GC at the end of the 18 hour run. The GC analyses showed a total of 51 millimoles of propylene oxide in the gas phase and 4.5 millimoles of PO in the form of propylene glycol is formed in the liquid phase.

Run 2B: Epoxidation using Catalyst 1C and TS-1 with a Cesium Phosphate Buffer

Epoxidation is run according to the same procedure as Run 2A using catalyst 1C (0.2 g) in place of catalyst 1A. The GC analyses showed a total of 26 millimoles of propylene oxide in the gas phase and 2.3 millimoles of PO in the form of propylene glycol is formed in the liquid phase.

EXAMPLE 3

EPOXIDATION OF PROPYLENE USING TS-1 and $Pd/Nb_2O_5$ MIXTURE WITHOUT BUFFER Run 3A: Epoxidation is run according to the same procedure as Run 2A except that no buffer is used and the amounts of catalyst 1A (0.5 g), TS-1 (1 g), and deionized water (130 g) are different. The GC analyses showed a total of 11 millimoles of propylene oxide in the gas phase and 52 millimoles of PO in the form of propylene glycol is formed in the liquid phase.

Run 3B: Epoxidation is run according to the same procedure as Run. 2A using catalyst 1A (0.2 g), TS-1 (0.5 g), and 130 grams of deionized water, except that no buffer is used. The GC analyses showed a total of 8.6 millimoles of propylene oxide in the gas phase and 25 millimoles of PO in the form of propylene glycol is formed in the liquid phase.

The epoxidation results show that the use of a TS-1 and Pd/Nb$_2$O$_5$ catalyst mixture leads to the production of propylene oxide (PO) and PO equivalents in the form of propylene glycol (PG) in high yield. The use of a buffered solution improves the selectivity to propylene oxide, with less unwanted glycol formation.

I claim:

1. A process for producing an epoxide comprising reacting an olefin, hydrogen and oxygen in an oxygenated solvent in the presence of a catalyst mixture comprising a titanium zeolite and a supported catalyst comprising palladium and a support, wherein the support is an inorganic oxide containing niobium.

2. The process of claim 1 wherein the titanium zeolite is titanium silicalite.

3. The process of claim 1 wherein the titanium zeolite is TS-1.

4. The process of claim 1 wherein the supported catalyst is comprised of from 0.01 to 10 weight percent palladium.

5. The process of claim 1 wherein the support is Nb$_2$O$_5$ or niobium oxide-silica.

6. The process of claim 1 wherein the support is Nb$_2$O$_5$.

7. The process of claim 1 wherein the olefin is a C$_2$–C$_6$ olefin.

8. The process of claim 1 wherein the olefin is propylene.

9. The process of claim 1 wherein the oxygenated solvent is selected from the group consisting of water, C$_1$–C$_4$ alcohols, and mixtures thereof.

10. The process of claim 9 wherein the oxygenated solvent is water.

11. The process of claim 1 wherein the oxygenated solvent contains a buffer.

12. The process of claim 11 wherein the buffer is cesium phosphate.

13. The process of claim 1 further comprising a carrier gas.

14. The process of claim 13 wherein the carrier gas is selected from the group consisting of helium, neon, argon, nitrogen, carbon dioxide, and C$_{1-8}$ saturated hydrocarbons.

15. The process of claim 14 wherein the carrier gas is propane.

16. A process comprising reacting propylene, hydrogen and oxygen in water in the presence of a catalyst mixture comprising a titanium silicalite and a supported catalyst comprising palladium and Nb$_2$O$_5$.

17. The process of claim 16 wherein the titanium silicalite is TS-1.

18. The process of claim 16 wherein the supported catalyst is comprised of from 0.01 to 10 weight percent palladium.

19. The process of claim 16 wherein the water contains a buffer.

20. The process of claim 19 wherein the buffer is cesium phosphate.

* * * * *